US008962585B2

(12) United States Patent
Collard et al.

(10) Patent No.: US 8,962,585 B2
(45) Date of Patent: Feb. 24, 2015

(54) TREATMENT OF TUMOR PROTEIN 63 (P63) RELATED DISEASES BY INHIBITION OF NATURAL ANTISENSE TRANSCRIPT TO P63

(75) Inventors: Joseph Collard, Delray Beach, FL (US); Olga Khorkova Sherman, Tequesta, FL (US)

(73) Assignee: CuRNA, Inc., Miami, FL (US)

( * ) Notice: Subject to any disclaimer, the term of this patent is extended or adjusted under 35 U.S.C. 154(b) by 0 days.

(21) Appl. No.: 13/519,477

(22) PCT Filed: Dec. 29, 2010

(86) PCT No.: PCT/US2010/062326
§ 371 (c)(1),
(2), (4) Date: Jun. 27, 2012

(87) PCT Pub. No.: WO2011/090741
PCT Pub. Date: Jul. 28, 2011

(65) Prior Publication Data
US 2012/0295953 A1    Nov. 22, 2012

Related U.S. Application Data

(60) Provisional application No. 61/290,540, filed on Dec. 29, 2009.

(51) Int. Cl.
*C12N 15/11* (2006.01)
*C12N 15/113* (2010.01)
*A61K 31/7088* (2006.01)

(52) U.S. Cl.
CPC ........ *C12N 15/1135* (2013.01); *A61K 31/7088* (2013.01); *C12N 2310/11* (2013.01); *C12N 2310/315* (2013.01); *C12N 2310/113* (2013.01)
USPC ..................................................... 514/44 A

(58) Field of Classification Search
USPC ..................................................... 514/44 A
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,754,065 A | 6/1988 | Levenson et al. |
| 4,800,159 A | 1/1989 | Mullis et al. |
| 5,034,506 A | 7/1991 | Summerton et al. |
| 5,138,045 A | 8/1992 | Cook et al. |
| 5,218,105 A | 6/1993 | Cook et al. |
| 5,288,512 A | 2/1994 | Seiden |
| 5,288,514 A | 2/1994 | Ellman |
| 5,319,080 A | 6/1994 | Leumann |
| 5,393,878 A | 2/1995 | Leumann |
| 5,432,272 A | 7/1995 | Benner et al. |
| 5,457,189 A | 10/1995 | Crooke et al. |
| 5,459,255 A | 10/1995 | Cook et al. |
| 5,474,796 A | 12/1995 | Brennan |
| 5,491,084 A | 2/1996 | Chalfie et al. |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,576,302 A | 11/1996 | Cook et al. |
| 5,593,853 A | 1/1997 | Chen et al. |
| 5,605,662 A | 2/1997 | Heller et al. |
| 5,661,134 A | 8/1997 | Cook et al. |
| 5,708,161 A | 1/1998 | Reese |
| 5,739,119 A | 4/1998 | Galli et al. |
| 5,739,311 A | 4/1998 | Lackey et al. |
| 5,756,710 A | 5/1998 | Stein et al. |
| 5,849,902 A | 12/1998 | Arrow et al. |
| 5,891,725 A | 4/1999 | Soreq et al. |
| 5,902,880 A | 5/1999 | Thompson |
| 5,908,779 A | 6/1999 | Carmichael et al. |
| 5,965,721 A | 10/1999 | Cook et al. |
| 5,985,663 A | 11/1999 | Bennett et al. |
| 6,005,095 A | 12/1999 | Capaccioli et al. |
| 6,013,639 A | 1/2000 | Peyman et al. |
| 6,013,786 A | 1/2000 | Chen et al. |
| 6,034,233 A | 3/2000 | Ecker et al. |

(Continued)

FOREIGN PATENT DOCUMENTS

| | | |
|---|---|---|
| CA | 2686933 | 4/2008 |
| EP | 335451 A3 | 3/1988 |
| EP | 335451 A2 | 10/1989 |
| WO | WO-84/03564 | 9/1984 |
| WO | WO-91/19735 | 12/1991 |
| WO | WO-92/00091 | 1/1992 |
| WO | WO-92/08796 | 5/1992 |
| WO | WO-93/20242 | 10/1993 |
| WO | WO-94-26887 A1 | 11/1994 |
| WO | WO-94/28143 | 12/1994 |
| WO | WO-95-15373 A2 | 6/1995 |
| WO | WO-95/22618 | 8/1995 |
| WO | WO-95/25116 | 10/1995 |
| WO | WO-95/35505 | 12/1995 |

(Continued)

OTHER PUBLICATIONS

Czaudema et al. Nucleic Acid Research 31:2705-2716, 2003.*
Scheel et al. Cell Cycle 8:1426-1432, May 2009.*
He et al. disclose that the distribution of antisense transcripts was distinct from that of sense transcripts and differed among cell types (Science 2008, 322:1855-1857).*
Elsa Flores Cell Cycle 6:300-304, 2007.*
International Search Report corresponding to PCT/US2010/062326 dated Sep. 16, 2011.

(Continued)

*Primary Examiner* — Brian Whiteman
(74) *Attorney, Agent, or Firm* — CuRNA, Inc.; Monte R. Browder

(57) ABSTRACT

The present invention relates to antisense oligonucleotides that modulate the expression of and/or function of Tumor Protein 63 (p63), in particular, by targeting natural antisense polynucleotides of Tumor Protein 63 (p63). The invention also relates to the identification of these antisense oligonucleotides and their use in treating diseases and disorders associated with the expression of p63.

12 Claims, 1 Drawing Sheet

(56) References Cited

U.S. PATENT DOCUMENTS

| | | |
|---|---|---|
| 6,100,090 A | 8/2000 | Monia et al. |
| 6,140,492 A | 10/2000 | Morelli et al. |
| 6,147,200 A | 11/2000 | Manoharan et al. |
| 6,165,712 A | 12/2000 | Foulkes et al. |
| 6,165,990 A | 12/2000 | Singh et al. |
| 6,175,409 B1 | 1/2001 | Nielsen et al. |
| 6,221,587 B1 | 4/2001 | Ecker et al. |
| 6,239,265 B1 | 5/2001 | Cook |
| 6,242,589 B1 | 6/2001 | Cook et al. |
| 6,268,490 B1 | 7/2001 | Imanishi et al. |
| 6,303,374 B1 | 10/2001 | Zhang et al. |
| 6,307,040 B1 | 10/2001 | Cook et al. |
| 6,316,198 B1 | 11/2001 | Skouv et al. |
| 6,335,434 B1 | 1/2002 | Guzaev et al. |
| 6,376,541 B1 | 4/2002 | Nixon et al. |
| 6,403,566 B1 | 6/2002 | Wang |
| 6,444,464 B1 | 9/2002 | Wyatt |
| 6,451,991 B1 | 9/2002 | Martin et al. |
| 6,525,191 B1 | 2/2003 | Ramassamy |
| 6,528,262 B1 | 3/2003 | Gilad et al. |
| 6,528,631 B1 | 3/2003 | Cook et al. |
| 6,617,122 B1 | 9/2003 | Hayden et al. |
| 6,617,442 B1 | 9/2003 | Crooke et al. |
| 6,630,315 B1 | 10/2003 | Miwa et al. |
| 6,639,059 B1 | 10/2003 | Kochkine et al. |
| 6,656,730 B1 | 12/2003 | Manoharan |
| 6,667,337 B2 | 12/2003 | Wilson |
| 6,670,461 B1 | 12/2003 | Wengel et al. |
| 6,710,174 B2 | 3/2004 | Bennett et al. |
| 6,734,291 B2 | 5/2004 | Kochkine et al. |
| 6,762,169 B1 | 7/2004 | Manoharan |
| 6,794,499 B2 | 9/2004 | Wengel et al. |
| 6,833,361 B2 | 12/2004 | Hong et al. |
| 6,861,514 B2 | 3/2005 | Cook et al. |
| 6,867,294 B1 | 3/2005 | Sanghvi et al. |
| 6,936,467 B2 | 8/2005 | Kmiec et al. |
| 6,936,593 B1 | 8/2005 | Agrawal et al. |
| 6,977,295 B2 | 12/2005 | Belotserkovskii et al. |
| 6,986,988 B2 | 1/2006 | Gilad et al. |
| 7,034,133 B2 | 4/2006 | Wengel et al. |
| 7,034,145 B2 | 4/2006 | Shen et al. |
| 7,053,195 B1 | 5/2006 | Goff |
| 7,053,199 B2 | 5/2006 | Imanishi et al. |
| 7,053,207 B2 | 5/2006 | Wengel |
| 7,060,809 B2 | 6/2006 | Wengel et al. |
| 7,084,125 B2 | 8/2006 | Wengel |
| 7,087,589 B2 | 8/2006 | Jacobson et al. |
| 7,125,982 B1 | 10/2006 | Frayne |
| 7,144,995 B2 | 12/2006 | Wise et al. |
| 7,144,999 B2 | 12/2006 | Ward et al. |
| 7,148,204 B2 | 12/2006 | Bennett et al. |
| 7,153,954 B2 | 12/2006 | Koch et al. |
| 7,169,916 B2 | 1/2007 | Krotz et al. |
| 7,199,107 B2 | 4/2007 | Dobie et al. |
| 7,202,357 B2 | 4/2007 | Crooke et al. |
| 7,217,572 B2 | 5/2007 | Ward et al. |
| 7,220,549 B2 | 5/2007 | Buzby |
| 7,226,785 B2 | 6/2007 | Kmiec et al. |
| 7,229,974 B2 | 6/2007 | Peyman et al. |
| 7,229,976 B2 | 6/2007 | Dobie et al. |
| 7,235,534 B2 | 6/2007 | Tanguay et al. |
| 7,235,653 B2 | 6/2007 | Bennett et al. |
| 7,238,858 B2 | 7/2007 | Marraccini et al. |
| 7,276,599 B2 | 10/2007 | Moore et al. |
| 7,285,288 B1 | 10/2007 | Tormo et al. |
| 7,297,786 B2 | 11/2007 | McCray et al. |
| 7,314,923 B2 | 1/2008 | Kaneko et al. |
| 7,320,965 B2 | 1/2008 | Sah et al. |
| 7,321,828 B2 | 1/2008 | Cowsert et al. |
| 7,335,764 B2 | 2/2008 | Crooke et al. |
| 7,335,765 B2 | 2/2008 | Kaneko et al. |
| 7,339,051 B2 | 3/2008 | Crooke et al. |
| 7,371,833 B1 | 5/2008 | Weiss |
| 7,399,845 B2 | 7/2008 | Seth et al. |
| 7,402,434 B2 | 7/2008 | Newman et al. |
| 7,402,574 B2 | 7/2008 | Iversen et al. |
| 7,420,050 B2 | 9/2008 | Park et al. |
| 7,423,142 B2 | 9/2008 | Vornlocher |
| 7,425,545 B2 | 9/2008 | Crooke et al. |
| 7,427,675 B2 | 9/2008 | Capaldi et al. |
| 7,456,154 B2 | 11/2008 | Soreq et al. |
| 7,462,642 B2 | 12/2008 | Wang et al. |
| 7,468,431 B2 | 12/2008 | Bhanot et al. |
| 7,510,830 B2 | 3/2009 | Baguley et al. |
| 7,541,344 B2 | 6/2009 | Bhat et al. |
| 7,547,684 B2 | 6/2009 | Seth et al. |
| 7,569,575 B2 | 8/2009 | Sorensen et al. |
| 7,569,686 B1 | 8/2009 | Bhat et al. |
| 7,572,582 B2 | 8/2009 | Wengel et al. |
| 7,582,745 B2 | 9/2009 | Sah et al. |
| 7,585,893 B2 | 9/2009 | Baguley et al. |
| 7,589,190 B2 | 9/2009 | Westergaard et al. |
| 7,598,227 B2 | 10/2009 | Crooke et al. |
| 7,605,251 B2 | 10/2009 | Tan et al. |
| 7,622,453 B2 | 11/2009 | Frieden et al. |
| 7,662,948 B2 | 2/2010 | Kurreck et al. |
| 7,666,854 B2 | 2/2010 | Seth et al. |
| 7,674,895 B2 | 3/2010 | Reich et al. |
| 7,687,617 B2 | 3/2010 | Thrue et al. |
| 7,691,995 B2 | 4/2010 | Zamore et al. |
| 7,695,902 B2 | 4/2010 | Crooke |
| 7,696,345 B2 | 4/2010 | Allerson et al. |
| 7,709,456 B2 | 5/2010 | Corey et al. |
| 7,709,630 B2 | 5/2010 | Gaarde et al. |
| 7,713,738 B2 | 5/2010 | Hansen et al. |
| 7,718,629 B2 | 5/2010 | Bamcrot et al. |
| 7,723,508 B2 | 5/2010 | Crooke et al. |
| 7,732,422 B2 | 6/2010 | Gleave et al. |
| 7,732,590 B2 | 6/2010 | Bhanot et al. |
| 7,737,264 B2 | 6/2010 | Thrue et al. |
| 7,737,265 B2 | 6/2010 | Akinc et al. |
| 7,741,305 B2 | 6/2010 | Crooke et al. |
| 7,741,309 B2 | 6/2010 | Hansen et al. |
| 7,741,457 B2 | 6/2010 | Seth et al. |
| 7,745,609 B2 | 6/2010 | Bennett et al. |
| 7,749,978 B2 | 7/2010 | Sah et al. |
| 2003/0139359 A1 | 7/2003 | Dobie |
| 2003/0186920 A1 | 10/2003 | Sirois |
| 2003/0191075 A1 | 10/2003 | Cook et al. |
| 2003/0228618 A1 | 12/2003 | Levanon et al. |
| 2003/0233670 A1 | 12/2003 | Edgerton et al. |
| 2004/0006031 A1 | 1/2004 | Dean et al. |
| 2004/0033480 A1 | 2/2004 | Wong |
| 2004/0048254 A1 | 3/2004 | Olek et al. |
| 2004/0101858 A1 | 5/2004 | Ward et al. |
| 2004/0137423 A1 | 7/2004 | Hayden et al. |
| 2004/0138155 A1 | 7/2004 | Baird et al. |
| 2004/0175803 A1 | 9/2004 | Meritet et al. |
| 2004/0180336 A1 | 9/2004 | Gilad et al. |
| 2004/0228866 A1 | 11/2004 | Lu |
| 2004/0254137 A1 | 12/2004 | Ackermann et al. |
| 2005/0009771 A1 | 1/2005 | Levanon et al. |
| 2005/0026160 A1 | 2/2005 | Allerson et al. |
| 2005/0113326 A1 | 5/2005 | Siwkowski et al. |
| 2005/0143357 A1 | 6/2005 | Pousette et al. |
| 2005/0153286 A1 | 7/2005 | Clements |
| 2005/0215504 A1 | 9/2005 | Bennett et al. |
| 2005/0222029 A1 | 10/2005 | Bartel et al. |
| 2006/0009410 A1 | 1/2006 | Crooke et al. |
| 2006/0142196 A1 | 6/2006 | Klein et al. |
| 2006/0178333 A1 | 8/2006 | Soreq et al. |
| 2007/0082848 A1 | 4/2007 | Alitalo et al. |
| 2007/0197459 A1 | 8/2007 | Milner |
| 2007/0213274 A1 | 9/2007 | Salonen |
| 2007/0213292 A1 | 9/2007 | Stoffel et al. |
| 2007/0231816 A1 | 10/2007 | Chaussabel et al. |
| 2007/0248590 A1 | 10/2007 | Milne et al. |
| 2008/0146788 A1 | 6/2008 | Bhat et al. |
| 2008/0200664 A1* | 8/2008 | Yang et al. .......... 536/23.5 |
| 2008/0221051 A1 | 9/2008 | Becker et al. |
| 2008/0293142 A1 | 11/2008 | Liu et al. |
| 2009/0191263 A1 | 7/2009 | Reich et al. |
| 2009/0192106 A1 | 7/2009 | Dobie et al. |
| 2009/0208479 A1 | 8/2009 | Jaye et al. |

(56) References Cited

U.S. PATENT DOCUMENTS

| | | |
|---|---|---|
| 2009/0258925 A1 | 10/2009 | Wahlestedt |
| 2009/0318536 A1 | 12/2009 | Freier et al. |
| 2009/0326041 A1 | 12/2009 | Bhanot et al. |
| 2010/0105760 A1 | 4/2010 | Collard et al. |

FOREIGN PATENT DOCUMENTS

| | | |
|---|---|---|
| WO | WO-96-27663 A2 | 9/1996 |
| WO | WO-97-39120 A1 | 10/1997 |
| WO | WO-99-14226 A1 | 3/1999 |
| WO | 9919357 A1 | 4/1999 |
| WO | WO-99-39352 A1 | 8/1999 |
| WO | WO-00-57837 A1 | 10/2000 |
| WO | WO-00-61770 A2 | 10/2000 |
| WO | WO-01-00669 A2 | 1/2001 |
| WO | WO-01-21631 A2 | 3/2001 |
| WO | WO-01-25488 A2 | 4/2001 |
| WO | WO-01-51630 A1 | 7/2001 |
| WO | WO-02-062840 A1 | 8/2002 |
| WO | WO-02-068688 A1 | 9/2002 |
| WO | 03004513 A1 | 1/2003 |
| WO | 03048315 A2 | 6/2003 |
| WO | WO-2004-016255 A1 | 2/2004 |
| WO | WO-2004-024079 A2 | 3/2004 |
| WO | WO-2004-030750 A1 | 4/2004 |
| WO | WO-2004-041838 A1 | 5/2004 |
| WO | WO-2004-104161 A2 | 12/2004 |
| WO | WO-2005-045034 A2 | 5/2005 |
| WO | WO-2005-070136 A2 | 8/2005 |
| WO | WO-2005-079862 A1 | 9/2005 |
| WO | WO-2007-028065 A2 | 3/2007 |
| WO | WO-2007-071182 A1 | 6/2007 |
| WO | WO-2007-087113 A2 | 8/2007 |
| WO | WO-2007-138023 A1 | 12/2007 |
| WO | 2008045344 A2 | 4/2008 |
| WO | WO-2008-057556 A2 | 5/2008 |
| WO | WO-2008-066672 A2 | 6/2008 |
| WO | WO-2008-087561 A2 | 7/2008 |
| WO | WO-2010-002984 A1 | 1/2010 |
| WO | WO-2010-040571 A2 | 4/2010 |
| WO | WO-2010-054364 A1 | 5/2010 |
| WO | WO-2010-058227 A2 | 5/2010 |

OTHER PUBLICATIONS

Ausubel, Current Protocols in Molecular Biology vol. 1, 1994, 6.0.1-6.4.10.
Barak, et al., "A β-Arrestin/Green Fluorescent Protein Biosensor for Detecting G Protein-Coupled Receptor Activation," J. Biol. Chem. 272:27497-27500 (1997).
Barber, et al., "Delivery of membrane-impermeant fluorescent probes into living neural cell populations by lipotransfer," Neuroscience Letters 207:17-20 (1996).
Baum, "Solid-phase synthesis of benzodiazepines," C&EN News, Jan. 18, p. 33-34 (1993).
Bernstein, E., et al., "Role for a bidentate ribonuclease in the initiation step of RNA interference," Nature 409:363 (2001).
Boutla, A., et al., "Short 5'-phosphorylated double-stranded RNAs induce RNA interference in *Drosophila*," Curr. Biol. 11:1776-1780 (2001).
Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).
Brazma & Vilo, "Gene Expression data analysis," FEBS Lett., 480:17-24 (2000).
Bright, et al., "Chapter 6. Fluorescence Ratio Imaging Microscopy," Methods in Cell Biology vol. 30, Taylor and Wang (eds) p. 157-192 (1989).
Bright, et al., "Delivery of Macromolecules Into Adherent Cells via Electroporation for Use in Fluorescence Spectroscopic Imaging and Metabolic Studies," Cytometry 24:226-233 (1996).
Bright, et al., "Fluorescence Ratio Imaging Microscopy: Temporal and Spatial Measurements of Cytoplasmic pH," J. Cell Biology 104:1019-1033 (1987).
Campbell, et al., "Phosphonmate Ester Synthesis Using a Modified Mitsunobu Condensation," J. Org. Chem. 59:658-660 (1994).
Caplen, N. J., et al., "Specific inhibition of gene expression by small double-stranded RNAs in invertebrate and vertebrate systems," PNAS Sci. USA 98:9742-9747 (2001).
Carninci, et al., "The transcriptional landscape of the mammalian genome," Science 309:1559-1563 (2005).
Carulli, et al., "High Throughput Analysis of Differential Gene Expression," J. Cell Biochem. Suppl., 3:286-296 (1998).
Celis, et al., "Gene expression profiling: monitoring transcription and translation products using DNA microarrays and proteomics," FEBS Lett., 480:2-16 (2000).
Chabala, J.C., "Solid-phase combinatorial chemistry and novel tagging methods for identifying leads," Curr Opin Biotechnol, 6:632-639 (1995).
Cech, J., "Ribozymes and Their Medical Implications," American. Med Assoc. 260:3030-3035 (1988).
Chen, et al., "Expression of ssDNA in Mammalian Cells," BioTechniques 34:167-171 (2003).
Chen, et al., "Analogous Organic Synthesis of Small-Compound Libraries: Validation of Combinatorial Chemistry in Small-Molecule Synthesis," J. Amer. Chem. Soc. 116:2661-2662 (1994).
Cheng, J. et al., "Transcriptional maps of 10 human chromosomes at 5-nucleotide resolution," Science 308:5725:1149-1154 (2005).
Cho, et al., "An Unnatural Biopolymer," Science 261:1303-1305 (1993).
Christiensen, N.K. et al., "A Novel Class of Oligonucleotide Analogues Containing 2'-O,3'-C-Linked [3.2.0]Bicycloarabinonucleoside Monomers: Synthesis, Thermal Affinity Studies, and Molecular Modeling," J. Am. Chem. Soc., 120:5458-5463 (1998).
Cubitt, et al., "Understanding, improving and using green fluorescent proteins," Trends in Biochemical Science 20:448-455 (1995).
Curiel, D. T. et al., "Adenovirus enhancement of transferrin-polylysine-mediated gene delivery," PNAS 88:8850-8854 (1991).
Dai et al., "SIRTI Interacts With p73 and Suppresses p73-Dependent Transcriptional Activity," J Cell Physiol 210(1):161-165 (2007).
Davidson, et al., "A model system for in vivo gene transfer into the central nervous system using an adenoviral vector," Nat. Genet 3:219-223 (1993).
Davis, et al., "Direct Gene Transfer into Skeletal Muscle In Vivo: Factors Affecting Efficiency of Transfer and Stability of Expression," Hum Gene Ther 4:151-159 (1993).
De Mesmaeker, et al., "Antisense Oligonucleotides," Acc. Chem. Res. 28:366-374 (1995).
Deng et al., "Small Interfering RNA Targeting the PINK1 Induces Apoptosis in Dopaminergic Cells SH-SY5Y", Biochemical and Biophysical Research Communications, vol. 337, No. 4, pp. 1133-1138 (2005).
Dixon, et al., "Anthrax," New England J. Med. 341:815-826 (1999).
Dolle, "Discovery of Enzyme inhibitors through combinatorial chemistry," Mol Divers. 2:223-236 (1997).
Eguchi, et al., "Antisense RNA," Annu. Rev. Biochem 60:631-652 (1991).
Eichler, et al., "Generation and utilization of synthetic combinatorial libraries," Mol Med Today 1:174-180 (1995).
Eichler et al., "Peptide Peptidomimetic and organic synthetic combinatorial libraries," Med Res Rev 15:481-496 (1995).
Espeseth, et al., A genome wide analysis of ubiquitin ligases in APP processing identifies a novel regulator of BACE1 mRNA levels, Mol. Cell Neurosci. 33: 227-235 (2006).
Faghihi, M. & Wahlestedt C., "RNA interference is not involved in natural antisense mediated regulation of gene expression in mammals," Genome Biol (2005).
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).

(56) References Cited

OTHER PUBLICATIONS

Fields, et al., "How many genes in the human genome?" Nature Genetics 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res, 15:4513 (1987).
Geller, A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I. et al., "Long-term increases in neurotransmitter release from neuronal cells expressing a constitutively active adenylate cyclase from a herpes simplex virus type 1 vector," PNAS U.S.A.:90:7603-7607 (1993).
Geller, A.I., et al., "Infection of cultured central nervous system neurons with a defective herpes simplex virus 1 vector results in stable epression of *Escherichia coli* β-galactosidase," PNAS USA 87:1149-1153 (1990).
Giuliano, et al., "FLuorescent Protein Biosensors: Measurement of Molecular Dynamics in Living Cells," Ann. Rev. of Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).
Heller, et al., "Discovery and analysis of inflammatory disease-relate genes using cDNA microarrays," PNAS U.S.A. 94:2150-2155 (1997).
Herdewijn P., "Heterocyclic Modifications of Oligonucleotides and Antisense Technology," Antisense & Nucleic Acid Drug Dev., 10:297-310 (2000).
Hirschmann, et al., J. Amer. Chem. Soc., 114:9217-9218 (1992).
Hobbs-DeWitt, et al., "Diversomers: An approach to nonpeptide, nonoligomeric chemical diversity," Proc. Nat. Acad. Sci. USA 90;6909-6913 (1993).
Houghton AN, Gold JS, Blachere NE, Immunity against cancer: lessons learned from melanoma,. Curr Opin Immunol 13:134-140 (2001).
International Human Genome Sequencing Consortium "Finishing the euchromatic sequence of the human genome," Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigene RNAs," Nature Chemical Biology, 1(4):216-222 (2005).
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Microbiol., 3:316-321 (2000).
Kabanov, et al., "A new class of antivirals: antisense oligonucleotides combined with a hydrophobic substituent effectively inhibit influenza virus reproduction and synthesis of virus-specific proteins in MDCK cells," FEBS Lett 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification of enzyme inhibitors from phage-displayed combinatorial peptide libraries," Comb Chem High Throughput Screen 4:535-543 (2001).
Kenan, et al., "Exploring molecular diversity with combinatorial shape libraries," Trends Biochem Sci 19:57-64(1994).
Kornberg, A., DNA Replication, W.H. Freeman & Co., San Francisco, 1980 pp. 75-77.
Larson, et al., "Rapid DNA Fingerprinting of Pathogens by Flow Cytometry," Cytometry, 2000, 41:203-208 (2000).
Larsson, et al., "High-throughput protein expression of cDNA products as a tool in functional genomics," J. Biotechnology., 80:143-157 (2000).
Lebl, et al., "One-bead-one-structure combinatorial libraries," Biopolymers 37:177-198 (1995).
LeGal Lasalle et al., "An Adenovirus Vector for Gene Transfer into Neurons and Glia in teh Brain," Science 259:988-990 (1993).
Letsinger, et al., "Cholesteryl-conjugated oligonucleotides: Synthesis, properties, and activity as inhibitors of replication of human immunodeficiency virus in cell culture," PNAS 86:6553-6556 (1989).
Li et al., "Control of APP processing and Aβ generation level by BACE1 enzymatic activity and transcription," Faseb J 20; 285-292 (2006).
Li, et al., "Increased Plaque Burden in Brains of APP Mutant MnSOD Heterozygous Knockout Mice," J. Neurochem 89 1308-1312 (2004).
Liang, et al., "Parallel Synthesis and Screening of a Solid Phase Carbohydrate Library," Science 274:1520-1522 (1996).
Luther, "Role of endogenous analysis RNA in cardiac gene regulation," J. Mol. Med. 83:26-32 (2005).
Madden, et al., "Serial analysis of gene expression: from gene discovery to target identification," Drug Discov. Today 5:415-425 (2000).
Makalowska I, Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al., "Lipidic Nucleic Acids," Tetrahedron Lett 36:3651-3654 (1995).
Manoharan, et al., "Chemical Modifications to Improve Uptake and Bioavailability of Antisense Oligonucleotides," Ann. N.Y. Acad. Scie 660:306-309 (1992).
Manoharan, et al., "Introduction of a Lipophilic Thioether in teh Minor Groove of Nucleic Acids for Antisense Applications," Bioorg. Med. Chem. Let 3:2765-2770 (1993).
Manoharan, et al., "Cholic Acid-Oligonucleotide Conjugates for Antisense Applications," Bioorg. Med. Chem. Let 4;1053 (1994).
Manoharan, et al., "Oligonucleotide Conjugates: Alteration of the Pharmacokinetic Properties of Antisense Agents," Nucleosides & Nucleotides 14:969-973 (1995).
Manoharan, M., "2'-Carbohydrate modifications in antisense oligonucleotide therapy: importance of conformation, configurationj and conjugation," Biochemica et Biophysica Acta 1489:117-139 (1999).
Mattick, J. S. "RNA regulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).
McNeil in Methods in Cell Biology vol. 29, Taylor and Wang (eds.) p. 153-173 (1989).
Morelli et al., "The antisense bcl-2-IgH transcript is an optimal target for synthetic oligonucleotides," PNAS USA 94:8150-8155 (1997).
Nielsen, et al., "Sequence-Selective Recognition of DNA by Strand Displacement with a Thymine-Substituted Polyamide," Science 254:1497-1500 (1991).

(56) References Cited

OTHER PUBLICATIONS

Oberhauser, et al., "Effective incorporation of 2'-O-methyl-oligoribonucleotides into liposomes and enhanced cell association through modification with thiocholesterol," Nucl. Acids Res. 20:533-538 (1992).
Petit et al., "Wild-type PINK1 Prevents Basal and Induced Neuronal Apoptosis, a Protective Effect Abrogated by Parkinson Disease-Related Mutations", Journ. Biol. Chem., vol. 280, No. 40, pp. 34025-334032 (2005).
Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis of Differential Gene Expression," Methods Enzymol., 303:258-272 (1999).
Quantin, et al., "Adenovirus as an expression vector in muscle cells in vivo," PNAS 89:2581-2584 (1992).
Rosenfeld, et al., "In Vivo Transfer of the Human Cystic Fibrosis Transmembrane Conductance Regulator Gene to the Airway Epithelium," Cell, 68:143-155 (1992).
Rosok and Sioud, "Systematic identification of sense-antisense transcripts in mammalian cells," Nature Biotech. 22(1):104-108 (2004).
Saison-Behmoaras, et al., "Short modified antisense oligonucleotides directed against Ha-ras point mutation induce selective cleavage of the mRNA and inhibit T24 cells proliferation," EMBO J. 10:1111-1118 (1991).
Sanghvi, Y.S., in Crooke, S.T. and Lebleu, B., eds., Antisense Research and Applications, CRC Press, Boca Raton, 1993, p. 276-278.
Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).
Schena, et al., "Parallel human genome analysis: Microarray-based expression monitoring of 1000 genes," PNAS 93:10614-10619(1996).
Shea, et al., "Synthesis, hybridization properties and antiviral activity of lipid-oligodeoxynucleotide conjugates," Nucl. Acids Res 18:3777-3783 (1990).
Shimomura, et al., "Semi-synthetic aequorin," J. of Biochemistry (Tokyo) 251:405-440 (1988).
Singer, et al., "Targeting BACE1 with siRNAs ameliorates Alzheimer disease neuropathology in a transgenic model," Nat Neurosci 8:1343-1349 (2005).
Southwick, et al., "Cyanine Dye Labeling Reagents-Carboxymethylindocyanine Succinimidyl Esters," Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun et al., "Downregulation of Sirt1 by antisense oligonucleotides induces apoptosis and enhances radiations sensitization in A549 lung cancer cells," Lung Cancer 58(1):21-29 (2007).
Sutcliffe, et al., "TOGA: An automated parsing technology for analyzing expression of nearly all genes," PNAS, 97:1976-1981 (2000).
Sutton, et al., "TIGR Assembler: A New Tool for Assembling Large Shotgun Sequencing Projects," Genome Science & Tech., 1:9-19 (1995).
Svinarchuk, et al., "Inhibition of HIV proliferation in MT-4 cells by antisense oligonucleotide conjugated to lipophilic groups," Biochimie 75:49-54 (1993).
Tamagno, et al., "The varions aggregation states of β-amyloid 1-42 mediate different effects on oxidative stress, neurodegeneration, and BACE-1 expression," Free Radic Biol Med 41:202-212 (2006).
Thakker, D.R., et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measurements in Ehrlich Ascites Tumor Cells Utilizing Spectroscopic Probes Generated in Situ," Biochemistry 18:2210-2218 (1979).
Thompson, et al., "Synthesis and Applications of Small Molecule Libraries" Chem Rev 96:555-600 (1996).
To, Ky, "Identification of Differential Gene Expressionm by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien in Methods in Cell Biology vol. 30 Taylor and Wang (eds) p. 127-156 (1989).
Ulhman, E., "Recent advances in the medical chemistry of antisense oligonucleotide," Current Opinions in Drug Discovery & Development 3:203-213 (2000).
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).
Vanhee-Brossolet and Vaquero, "Do natural antisense transcripts make sense in eukaryotes?" Gene 211:1-9 (1998).
Vaughn, et al., "Human Antibodies with Sub-nanomolar Affinities Isolated from a Large Non-immunized Phage Display Library," Nature Biotechnology, 14:3:309-314 (1996).
Velculescu, et al., "Serial Analysis of Gene Expression," Science 270:484-487 (1995).
Wahlestedt, "Natural antisense and noncoding RNA transcripts as potential drug targets," Drug Discovery Today 11 (11/12):503-508 (2006).
Wahlestedt, C., "Antisense oligonucleotide strategies in neuropharmacology," Trends Pharmacol Sci 15:2:42-46 (1994).
Walsh, et al., The role of all-derived oligomers of Aβ in Alzheimer's disease and avenues for therapeutic intervention, Biochem Soc Trans 33: 1087-1090 (2005).
Wang, B.B. et al., "Identification of a nuclear-specific cyclophilin which interacts with the proteinase inhibitor eglin c," Biochem J. 314 (Pt 1) 313-319 (1996).
Wiesenhofer et al., "Glial cell line-derived neurotrophic factor (GDNP) is a proliferation factor for rat C6 glioma cells: evidence from antisense experiments," Antisense & Nucleic Acid Drug Development 10(5):311-321.
Xue, et al., "Hypoxia and reoxygenation increased BACE1 mRNA and protein levels in human neuroblastoma SH-SY5Y cells," Neurosci Lett 405,231-235 (2006).
Yamada et al., "Endothelial Nitric-Oxide Synthase Antisense (NOS3AS) Gene Encodes an Autophagy-Related Protein (APG9-like2) Highly Expressed in Trophoblast" (2005).
Yang, et al., "Cellular and Humoral Immune Responses to Viral Antigens Create Barriers to Lung-Directed Gene Therapy with Recombinant Adenoviruses," J. Virol 69:2004-2015 (1995).
EP Application No. 06850393.7 Examination Report dated Oct. 18, 2011.
International Search Report and Written Opinion for PCT Application No. PCT/US2010/033078 mailed Jun. 29, 2011.
PCT/US2010/026119 Search Report and Written Opinion mailed Feb. 7, 2011.
PCT/US2010/024079 Search Report and Written Opinion mailed Jan. 31, 2011.
PCT/US2010/027394 Search Report and Written Opinion mailed Nov. 5, 2010.
PCT/US96/10287 (WO97/000271) The Regents of the University of California, Jan. 3, 1997.
Carroll, A. P., et al., "Design and Interpretation of MicroRNA—Reporter Gene Activity"; Analytical Biochemistry; vol. 437: 164-171, (2013).
Derrien, T., et al., "The GENCODE v7 Catalog of Human Long Noncoding RNAs: Analysis of Their Gene Structure, Evolution, and Expression"; Genome Research; vol. 22:1775-1789, (2012).

(56) References Cited

OTHER PUBLICATIONS

Jia, Wenwan, et al., "The Functions of MicroRNAs and Long Non-Coding RNAs in Embryonic and Induced Pluripotent Stem Cells"; Genomics, Proteomics & Bioinformatics; GPB 83, (2013).
Piao, H., et al., "Non-Coding RNAs as Regulators of Mammary Development and Breast Cancer"; J Mammary Gland Biol Neoplasia; NIH Public Access; vol. 17, Issue 1, pp. 33-42, (2012).
Levrero, M., et al., "The p53/p63/p73 Family of Transcription Factors: Overlapping and Distinct Functions," Journal of Cell Science, vol. 113, pp. 1661-1670, (2000).
Wang, D., et al., "Regulation of Limbal Keratinocyte Proliferation and Differentiation by TAp63 and ΔNp63 Transcription Factors," Investigative Ophthalmology & Visual Science, vol. 46, No. 9, pp. 3102-3108, (2005).
Moll, U., et al., "p63 and p73: Roles in Development and Tumor Formation," Mol Cancer Res, vol. 2, No. 7, pp. 371-386, (2004).
Murray-Zmijewski, F., et al., "p53/p63/p73 Isoforms: An Orchestra of Isoforms to Harmonise Cell Differentiation and Response to Stress," Cell Death and Differentiation, vol. 13, pp. 962-972, (2006).
Martin, M. A., et al., "Protection of Human HepG2 Cells Against Oxidative Stress by Cocoa Phenolic Extract," Journal of Agricultural and Food Chemistry, vol. 56, No. 17, pp. 7765-7772, (2008).
Senn, J., et al., "Interleukin-6 Induces Cellular Insulin Resistance in Hepatocytes," Diabetes, vol. 51, pp. 3391-3399, (2002).
Sabbisetti, V., et al., et al., "p63 Promotes Cell Survival Through Fatty Acid Synthase," PLoS ONE vol. 4, No. 6, e5877, pp. 1-13, (2009).
Kommagani, R., et al., "Regulation of VDR by ΔNp63α is Associated with Inhibition of Cell Invasion," J Cell Sci., vol. 122, No. 16, pp. 2828-2835, (2009).
Crum, C. P., et al., "p63 in Epithelial Survival, Germ Cell Surveillance, and Neoplasia," Annual Review of Pathology: Mechanisms of Disease, vol. 5, pp. 349-371, (2010). (Abstract).
Deutsch, G. B., et al., "DNA Damage in Oocytes Induces a Switch of the Quality Control Factor TAp63a from Dimer to Tetramer," Cell, vol. 144(4), pp. 566-576, (2011).
Dykxhoorn, D., et al., "Determinants of Specific RNA Interference-Mediated Silencing of Human β-Globin Alleles Differing by a Single Nucleotide Polymorphism," PNAS, vol. 103, No. 15, pp. 5953-5958, (2006).
GenBank Accession No. NM_000559, *Homo sapiens* Hemoglobin, Gamma A (HBG1), mRNA, (2008).
GenBank Accession No. NM_001114979.1, *Homo sapiens* Tumor Protein p63 (TP63), Transcript Variant 3, mRNA, (2014).
Ghioni, P., et al., "Complex Transcriptional Effects of p63 Isoforms: Identification of Novel Activation and Repression Domains," Molecular and Cellular Biology, vol. 22, No. 24, (2002).
Gu, J., "Mouse p63 Variants and Chondrogenesis," Int J Clin Exp Pathol, vol. 6(12), pp. 2872-2879, (2013).
Haussecker, D., et al., "Dicer-Dependent Turnover of Intergenic from the Human β-Globin Gene Cluster," Molecular and Cellular Biology, vol. 25, No. 21, pp. 9724-9733, (2005).
Humphries, L.A., et al., "Pro-apoptolic TP53 Homolog TAp63 is Repressed via Epigenetic Silencing and B-cell Receptor Signalling in Chronic Lymphocytic Leukaemia," Br J Haematol, vol. 163(5), pp. 590-602, (2013). (Abstract).
Melino, G., "p63 is a Suppressor of Tumorigenesis and Metastasis Interacting with Mutant p53," Cell Death and Differentiation, vol. 18, pp. 1487-1499, (2011).
Ramsey, M. R., "FGFR2 Signaling Underlies p63 Oncogenic Function in Squamous Cell Carcinoma," The Journal of Clinical Investifgation, vol. 123, No. 8, pp. 3525-3538. (2013). (Abstract).
Scheel, A. H., et al., "Immunofluorescence-Based Screen Identifies Germ Cell Associated microRNA 302 as an Antagonist to p63 Expression," Cell Cycle, vol. 8, No. 9, pp. 1426-1432, (2009).
Senoo, M., et al. "TAp63g (p51A) and dNp63a (p73L). Two Major Isoforms of the p63 Gene, Exert Opposite Effects on the Vascular Endothelial Growth Factor (VEGF) Gene Expression," Oncogene, vol. 21, pp. 2455-2465, (2002).
Shen, T., et al., "Modification of Globin Gene Expression by RNA Targeting Strategies," Experimental Hematology, vol. 35, No. 8, pp. 1209-1218, (2007).
Tadeu, A. M., et al., "Notch Signaling Represses p63 Expression in the Developing Surface Ectoderm," Stem Cells and Regeneration, Development, vol. 140, pp. 3777-3766, (2013). (Abstract).
Warner, S. M., et al., "Transcription Factor p63 Regulates Key Genes and Wound Repair in Human Airway Epithelial Basal Cell, Am J Respir Cell Mol Biol, vol. 49(6), pp. 978-988, (2013). (Abstract).

* cited by examiner

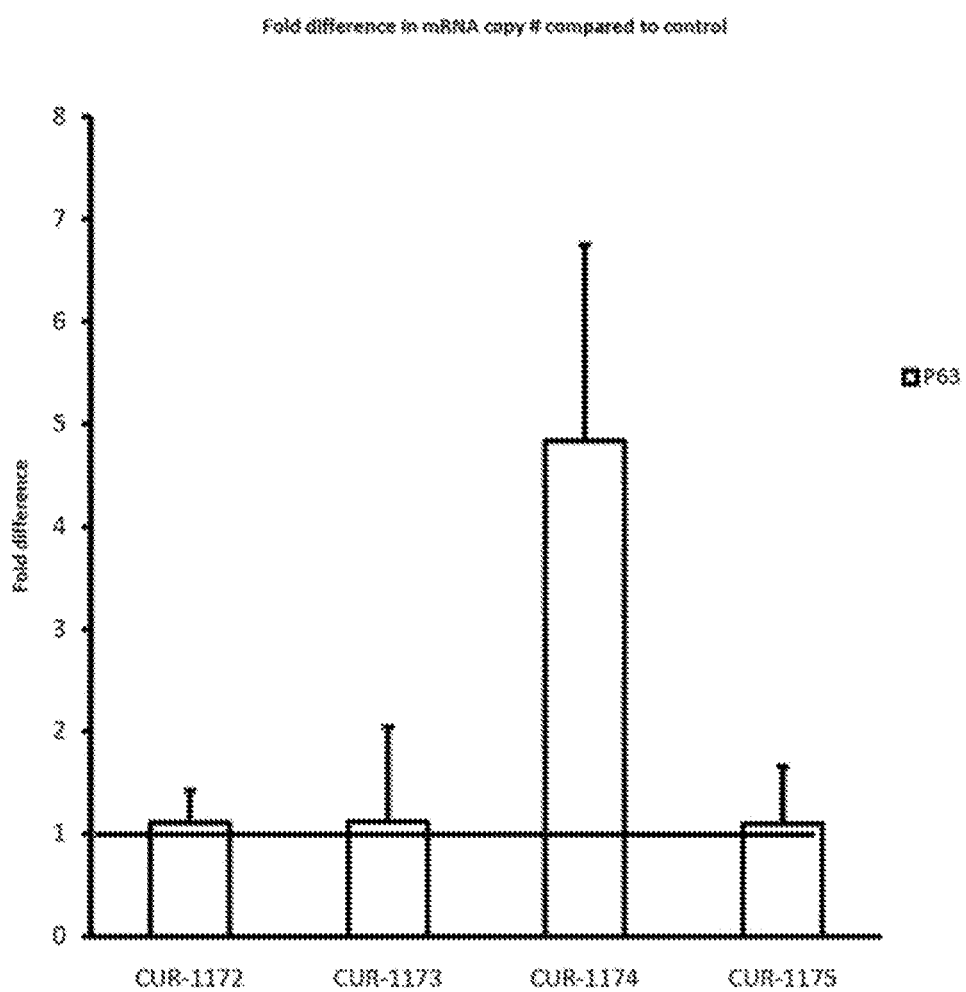

```
                           SEQUENCE LISTING

<160> NUMBER OF SEQ ID NOS: 6

<210> SEQ ID NO 1
<211> LENGTH: 2870
<212> TYPE: DNA
<213> ORGANISM: Homo sapiens
<300> PUBLICATION INFORMATION:
<308> DATABASE ACCESSION NUMBER: NM_001114979
<309> DATABASE ENTRY DATE: 2010-12-19
<313> RELEVANT RESIDUES IN SEQ ID NO: (1)..(2870)

<400> SEQUENCE: 1
cccggcttta tatctatata tacacaggta tatgtgtata ttttatataa ttgttctccg      60
ttcgttgata tcaaagacag ttgaaggaaa tgaattttga aacttcacgg tgtgccaccc     120
tacagtactg ccctgaccct tacatccagc gtttcgtaga aacccagct catttctctt     180 ggaaagaaag ttattaccga tccaccatgt cccagagcac acagacaaat gaattcctca     240
gtccagaggt tttccagcat atctgggatt ttctggaaca gcctatatgt tcagttcagc     300
ccattgactt gaactttgtg gatgaaccat cagaagatgg tgcgacaaac aagattgaga     360
ttagcatgga ctgtatccgc atgcaggact cggacctgag tgaccccatg tggccacagt     420
acacgaacct ggggctcctg aacagcatgg accagcagat tcagaacggc tcctcgtcca     480
ccagtcccta taacacagac cacgcgcaga acagcgtcac ggcgccctcg ccctacgcac     540
agcccagctc caccttcgat gctctctctc catcacccgc catccctcc aacaccgact     600 acccaggccc gcacagtttc gacgtgtcct tccagcagtc gagcaccgcc aagtcggcca     660
cctggacgta ttccactgaa ctgaagaaac tctactgcca aattgcaaag acatgcccca     720
tccagatcaa ggtgatgacc ccacctcctc agggagctgt tatccgcgcc atgcctgtct     780
acaaaaaagc tgagcacgtc acggaggtgg tgaagcggtg ccccaaccat gagctgagcc     840
gtgaattcaa cgagggacag attgcccctc ctagtcattt gattcgagta gaggggaaca     900
gccatgccca gtatgtagaa gatccatca caggaagaca gagtgtgctg gtaccttatg     960 agccaccccca ggttggcact gaattcacga cagtcttgta caatttcatg tgtaacagca    1020
gttgtgttgg agggatgaac cgccgtccaa tttttaatcat tgttactctg gaaaccagag    1080
atgggcaagt cctgggccga cgctgctttg aggcccggat ctgtgcttgc ccaggaagag    1140
acaggaaggc ggatgaagat agcatcagaa agcagcaagt ttcggacagt acaaagaacg    1200
gtgatggtac gaagcgcccg tttcgtcaga acacacatgg tatccagatg acatccatca    1260
agaaacgaag atccccagat gatgaactgt tatacttacc agtgagggggc cgtgagactt    1320 atgaaatgct gttgaagatc aaagagtccc tggaactcat gcagtaccct cctcagcaca    1380
caattgaaac gtacaggcaa cagcaacagc agcagccacca gcacttactt cagaaacatc    1440
tcctttcagc ctgcttcagg aatgagcttg tggagccccg gagagaaact ccaaaacaat    1500
ctgacgtctt ctttagacat tccaagcccc caaaccgatc agtgtaccca tagagcccta    1560
tctctatatt ttaagtgtgt gtgttgtatt tccatgtgta tatgtgagtg tgtgtgtgtg    1620
tatgtgtgtg cgtgtgtatc tagccctcat aaacaggact tgaagacact ttggctcaga    1680
gacccaactg ctcaaaggca caaagccact agtgagagaa tcttttgaag ggactcaaac    1740
```

```
ctttacaaga aaggatgttt tctgcagatt ttgtatcctt agaccggcca ttggtgggtg    1800
aggaaccact gtgtttgtct gtgagctttc tgttgtttcc tgggagggag gggtcaggtg    1860
gggaaggggg cattaagatg tttattggaa ccctttcctg tcttcttctg ttgttttct    1920 aaaattcaca gggaagcttt tgagcaggtc tcaaacttaa gatgtctttt taagaaaagg    1980
agaaaaaagt tgttattgtc tgtgcataag taagttgtag gtgactgaga gactcagtca    2040 gacccttta atgctggtca tgtaataata ttgcaagtag taagaaacga aggtgtcaag    2100
tgtactgctg ggcagcgagg tgatcattac caaaagtaat caactttgtg ggtggagagt    2160
tctttgtgag aacttgcatt atttgtgtcc tcccctcatg tgtaggtaga acatttctta    2220
atgctgtgta cctgcctctg ccactgtatg ttggcatctg ttatgctaaa gttttcttg    2280 tacatgaaac cctggaagac ctactacaaa aaaactgttg tttggccccc atagcaggtg    2340
aactcatttt gtgcttttaa tagaaagaca aatccacccc agtaatattg cccttacgta    2400
gttgtttacc attattcaaa gctcaaaata gaatttgaag ccctctcaca aaatctgtga    2460
ttaatttgct taattagagc ttctatccct caagcctacc taccataaaa ccagccatat    2520
tactgatact gttcagtgca tttagccagg agacttacgt tttgagtaag tgagatccaa    2580
gcagacgtgt taaaatcagc actcctggac tggaaattaa agattgaaag ggtagactac    2640
tttctttttt tttactcaaa agtttagaga atctctgttt cttttccattt taaaaacata    2700 ttttaagata atagcataaa gactttaaaa atgttcctcc cctccatctt cccacaccca    2760
gtcaccagca ctgtatttc tgtcaccaag acaatgattt cttgttattg aggctgttgc    2820
ttttgtggat gtgtgatttt aatttcaat aaacttttgc atcttggttt                  2870
```

```
<210> SEQ ID NO 2
<211> LENGTH: 288
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 2
```

```
cctagnatat acgggtcttg ctgtgttgcc ctgactggtc tcaaactgct ggactcaagc    60
tatcctcccg acccggcttc ccaaagtgtt gggattacag gcatgagcca ccacactcat    120
ctattttttt aaaaaattta aaaggtttat agcctaacgt atttaaataa taccatttaa    180
acgtatgtca tgatttcaat agttgttatt taaaaatcct aaagttacta agctaagagg    240
aacagaaatt aaatggcaac aaattttaaa taagtaaaaa aaaaaaaa                  288
```

```
<210> SEQ ID NO 3
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 3
gtccagcagt tgagaccag t                                                21
```

```
<210> SEQ ID NO 4
<211> LENGTH: 19
<212> TYPE: DNA
<213> ORGANISM: Artificial Sequence
<220> FEATURE:
<223> OTHER INFORMATION: Antisense oligonucleotide
```

-continued

```
<400> SEQUENCE: 4
tctgttcctc ttagcttag                                              19

<210> SEQ ID NO 5
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 5
ccagtcaggg caacacagca                                             20

<210> SEQ ID NO 6
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 6
gctcatgcct gtaatccca                                              19
```

TREATMENT OF TUMOR PROTEIN 63 (P63) RELATED DISEASES BY INHIBITION OF NATURAL ANTISENSE TRANSCRIPT TO P63

The present application claims the priority of U.S. provisional patent application No. 61/290,540 filed Dec. 29, 2009 which is incorporated herein by reference in its entirety.

FIELD OF THE INVENTION

Embodiments of the invention comprise oligonucleotides modulating expression and/or function of p63 and associated molecules.

BACKGROUND

DNA-RNA and RNA-RNA hybridization are important to many-aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE™ (for treatment of cytomegalovirus retinitis), reflecting that antisense has therapeutic utility.

SUMMARY

This Summary is provided to present a summary of the invention to briefly indicate the nature and substance of the invention. It is submitted with the understanding that it will not be used to interpret or limit the scope or meaning of the claims.

In one embodiment, the invention provides methods for inhibiting the action of a natural antisense transcript by using antisense oligonucleotide(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of an p63 polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within nucleotides 1 to 288 of SEQ ID NO: 2 thereby modulating function and/or expression of the p63 polynucleotide in patient cells or tissues in vivo or in vitro.

In an embodiment, an oligonucleotide targets a natural antisense sequence of p63 polynucleotides, for example, nucleotides set forth in SEQ ID NOS: 2, and any variants, alleles, homologs, mutants, derivatives, fragments and complementary sequences thereto. Examples of antisense oligonucleotides are set forth as SEQ ID NOS: 3 to 6.

Another embodiment provides a method of modulating function and/or expression of an p63 polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of the an antisense of the p63 polynucleotide; thereby modulating function and/or expression of the p63 polynucleotide in patient cells or tissues in vivo or in vitro.

Another embodiment provides a method of modulating function and/or expression of an p63 polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to an p63 antisense polynucleotide; thereby modulating function and/or expression of the p63 polynucleotide in patient cells or tissues in vivo or in vitro.

In an embodiment, a composition comprises one or more antisense oligonucleotides which bind to sense and/or antisense p63 polynucleotides.

In an embodiment, the oligonucleotides comprise one or more modified or substituted nucleotides.

In an embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including α-L-LNA.

In an embodiment, the oligonucleotides are administered to a patient subcutaneously, intramuscularly, intravenously or intraperitoneally.

In an embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In an embodiment, the oligonucleotides are encapsulated in a liposome or attached to a carrier molecule (e.g. cholesterol, TAT peptide).

Other aspects are described infra.

BRIEF DESCRIPTION OF THE DRAWINGS

FIG. 1 is a graph of real time PCR results showing the fold change+standard deviation in p63 mRNA after treatment of HEPG2 cells with phosphorothioate oligonucleotides introduced using Lipofectamine 2000, as compared to control. Real time PCR results show that the levels of p63 mRNA in HEPG2 cells are significantly increased 48 h after treatment with one of the oligos designed to p63 antisense. Bars denoted as CUR-1172, CUR-1173, CUR-1174, CUR-1175 correspond to samples treated with SEQ ID NOS 3, 4, 5 and 6 respectively.

Sequence Listing Description—SEQ ID NO: 1: Homo sapiens tumor protein p63 (Tp63), transcript variant 3, mRNA, mRNA. (NCBI Accession No.: NM_001114979); SEQ ID NO: 2: Natural p63 antisense sequence Hs.553263; SEQ ID NOs: 3 to 6—Antisense oligonucleotides. * indicates phosphothioate bond.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In an embodiment, the genes or nucleic acid sequences are human.

DEFINITIONS

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcripts) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA. An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoögsteen or reverse Hoögsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register", that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "p63" and "Tumor Protein 63" are inclusive of all family members, mutants, alleles, fragments, species, coding and noncoding sequences, sense and antisense polynucleotide strands, etc.

As used herein, the words Tumor protein 63, Tumor protein 63, Transformation-related protein 63, p63, p63, Tp63, AIS, B(p51A), B(p51B), Chronic ulcerative stomatitis protein, CUSP, EEC3, Keratinocyte transcription factor KET, KET, LMS, NBP, OFC8, p40, p51, p53CP, p73H, P73H, p73L, P73L, RHS, SHFM4, TP53CP, TP53L, TP73L and Tumor protein p73-like, are considered the same in the literature and are used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising prcmRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences. In certain embodiments of the present invention, the mediators are 5-25 nucleotide "small interfering" RNA duplexes (siRNAs). The siRNAs are derived from the processing of dsRNA by an RNase enzyme known as Dicer. siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion. Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarily to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity (Cech, (1988) *J. American. Med. Assoc.* 260, 3030-3035). Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA. This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphomates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner et al., U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties (sec e.g., described generally by Scheit, Nucleotide Analogs, John Wiley, New York, 1980: Freier & Altmann, (1997) *Nucl. Acid. Res.*, 25 (22), 4429-4443, Toulmé, J. J., (2001) *Nature Biotechnology* 19:17-18; Manoharan M., (1999) *Biochemica et Biophysica Acta* 1489:117-139; Freier S. M., (1997) *Nucleic Acid Research,* 25:4429-

4443, Uhlman, E., (2000) *Drug Discovery & Development*, 3: 203-213, Herdewin P., (2000) *Antisense & Nucleic Acid Drug Dev.*, 10:297-310); 2'-O, 3'-C-linked [3.2.0] bicycloarabinonucleosides. Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoögsteen or reversed Hoögsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the cast of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as Na++ or K++ (i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the an. Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.*, (1981) 2, 482-489).

As used herein, the term "Thermal Melting Point™" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant", when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides.

Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development, and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein, "cancer" refers to all types of cancer or neoplasm or malignant tumors found in mammals, including, but not limited to: leukemias, lymphomas, melanomas, carcinomas and sarcomas. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pincaloma, hemangioblastoma, acoustic neuroma, oligodendroglioma, meningioma, melanoma, neuroblastoma, and retinoblastoma. Additional cancers which can be treated by the disclosed composition according to the invention include but not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, gastric cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

Polynucleotide and Oligonucleotide Compositions and Molecules

Targets:

In one embodiment, the targets comprise nucleic acid sequences of Tumor Protein 63 (p63), including without limitation sense and/or antisense noncoding and/or coding sequences associated with p63.

Tumor protein 63 is a nuclear protein located on chromosome 3q, has been shown to possess homology with p53, a tumor-suppressor gene encoding a multi-functional DNA-binding protein important in cell cycle and cell death regulation. p63 exists in three isoforms, each of which can encode two categories of transcripts under the control of two alternative promoters. The first encodes full length proteins with an N-terminal transactivation domain that, like p53, can activate transcription and induce apoptosis. The second encodes truncated proteins lacking the N-terminal transactivation domain (ANp63), and potentially acting in a dominant-negative manner to suppress transactivation by p53 and/or full length p63.

In an embodiment, antisense oligonucleotides are used to prevent or treat diseases or disorders associated with p63 family members. Exemplary Tumor Protein 63 (p63) mediated diseases and disorders which can be treated with cell/tissues regenerated from stem cells obtained using the antisense compounds comprise: a disease or disorder associated with abnormal function and/or expression of p63, cancer, tumor, a proliferative disease or disorder, Corneal dystrophy, premature menopause, a disease or disorder associated with impaired hair growth cycle (e.g., alopecia etc.), a disease or disorder associated with impaired development of skin appendage (such as teeth, hair follicles, mammary, lacrimal and salivary glands, exocrine glands etc.), ectrodactyly-ectodermal dysplasia-cleft syndrome, Hay-Wells syndrome, limb mammary syndrome, a pulmonary disease or disorder, acrodermato-ungual-lacrimal-tooth syndrome, nonsyndromic split-hand/foot malformation, isolated cleft lip/palate, Rapp-Hodgkin syndrome, a skin disease or disorder (e.g., wound, alopecia (baldness), and a disease and disorder associated with aging and senescence.

In embodiments of the present invention, therapeutic and/or cosmetic regimes and related tailored treatments are provided to subjects requiring skin treatments or at risk of developing conditions for which they would require skin treatments. Diagnosis can be made, e.g., based on the subject's Tumor Protein 63 status. A patient's Tumor Protein 63 expression levels in a given tissue such as skin can be determined by methods known to those of skill in the art and described elsewhere herein, e.g., by analyzing tissue using PCR or antibody-based detection methods.

A preferred embodiment of the present invention provides a composition for skin treatment and/or a cosmetic application comprising Tumor Protein 63 antisense oligonucleotides, e.g., to upregulate expression of Tumor Protein 63 in the skin. Examples of antisense oligonucleotides are set forth as SEQ ID NOS: 3 to 6. U.S. Pat. No. 7,544,497, "Compositions for manipulating the lifespan and stress response of cells and organisms," incorporated herein by reference, describes potential cosmetic use for agents that modulate Tumor Protein 63 activity by reducing the $K_m$ of the Tumor Protein 63 protein for its substrate. In embodiments, cells art treated in vivo with the oligonucleotides of the present invention, to increase cell lifespan or prevent apoptosis. For example, skin can be protected from aging. e.g., developing wrinkles, by treating skin, e.g., epithelial cells, as described herein. In an exemplary embodiment, skin is contacted with a pharmaceutical or cosmetic composition comprising a Tumor Protein 63 antisense compound as described herein. Exemplary skin afflictions or skin conditions include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, skin cancer and the effects of natural aging.

In embodiments of the present invention, a composition comprising Tumor Protein 63 antisense oligonucleotides, e.g., to upregulate expression of Tumor Protein 63 in the scalp and inhibit androgen receptor signaling, thereby preventing androgenetic alopecia (hair loss). In embodiments, a patient suffering from alopecia is administered either a topical or systemic formulation.

In an embodiment, an antisense oligonucleotide described herein is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like. Formulations may be colorless, odorless ointments, lotions, creams, microemulsions and gels.

Antisense oligonucleotides of the invention may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington's Pharmaceutical Sciences (Mack Pub. Co.), ointment bases may be grouped into four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Exemplary water-soluble ointment bases are prepared from polyethylene glycols (PEGs) of varying molecular weight (see, e.g., Remington's, supra).

Antisense oligonucleotides of the invention may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. An exemplary lotion formulation for use in conjunction with the present method contains propylene glycol mixed with a hydrophilic petrolatum such as that which may be obtained under the trademark Aquaphor.sup® from Beiersdorf, Inc. (Norwalk, Conn.).

Antisense oligonucleotides of the invention may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

Antisense oligonucleotides of the invention may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifer") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., olcoyl macrogol glycerides), etc.

Antisense oligonucleotides of the invention may be incorporated into gel formulations, which generally are semisolid systems consisting of either suspensions made up of small inorganic particles (two-phase systems) or large organic molecules distributed substantially uniformly throughout a carrier liquid (single phase gels). Single phase gels can be made, for example, by combining the active agent, a earner liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives, known to those skilled in the art, may be included in formulations, e.g., topical formulations. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients and preservatives. An optimum topical formulation comprises approximately: 2 wt. % to 60 wt. %, preferably 2 wt. % to 50 wt. %, solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation.

A skin permeation enhancer serves to facilitate passage of therapeutic levels of active agent to pass through a reasonably sized area of unbroken skin. Suitable enhancers are well known in the art and include, for example: lower alkanols such as methanol ethanol and 2-propanol; alkyl methyl sulfoxides such as dimethylsulfoxide (DMSO), decylmethylsulfoxide ($C_{10}$ MSO) and tetradecylmethyl sulfoxide; pyrrolidones such as 2-pyrrolidone, N-methyl-2-pyrrolidone and N—(-hydroxyethyl)pyrrolidone; urea; N,N-diethyl-m-toluamide; $C_2$-$C_6$ alkanediols; miscellaneous solvents such as dimethyl formamide (DMF), N,N-dimethylacetamide (DMA) and tetrahydrofurfuryl alcohol; and the 1-substituted azacycloheptan-2-ones, particularly 1-n-dodecylcyclazacycloheptan-2-one (laurocapram; available under the trademark Azone.sup® from Whitby Research Incorporated, Richmond, Va.).

Examples of solubilizers include, but are not limited to, the following: hydrophilic ethers such as diethylene glycol monoethyl ether (ethoxydiglycol, available commercially as Transcutol.sup®) and diethylene glycol monoethyl ether oleate (available commercially as Soficutol.sup®); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as Labrasol.sup®); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in formulations, e.g., other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In an embodiment, modulation of p63 by one or more antisense oligonucleotides is administered to a patient in need thereof, for athletic enhancement and body building.

In an embodiment, modulation of p63 by one or more antisense oligonucleotides is administered to a patient in need thereof, to prevent or treat any disease or disorder related to p63 abnormal expression, function, activity as compared to a normal control.

In an embodiment, the oligonucleotides are specific for polynucleotides of p63, which includes, without limitation noncoding regions. The p63 targets comprise variants of p63; mutants of p63, including SNPs; noncoding sequences of p63; alleles, fragments and the like. Preferably the oligonucleotide is an antisense RNA molecule.

In accordance with embodiments of the invention, the target nucleic acid molecule is not limited to p63 polynucleotides alone but extends to any of the isoforms, receptors, homologs, non-coding regions and the like of p63.

In an embodiment, an oligonucleotide targets a natural antisense sequence (natural antisense to the coding and non-coding regions) of p63 targets, including, without limitation, variants, alleles, homologs, mutants, derivatives, fragments and complementary sequences thereto. Preferably the oligonucleotide is an antisense RNA or DNA molecule.

In an embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound. These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarily, is from about 80% to about 90%. In some embodiments, homology, sequence identity or complementarity, is about 90%, about 92%, about 94%, about 95%, about 96%, about 974, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In an embodiment, targeting of p63 including without limitation, antisense sequences which are identified and expanded, using for example, PCR, hybridization etc., one or more of the sequences set forth as SEQ ID NOS: 2, and the like, modulate the expression or function of p63. In one embodiment, expression or function is up-regulated as compared to a control. In an embodiment, expression or function is down-regulated as compared to a control.

In an embodiment, oligonucleotides comprise nucleic acid sequences set forth as SEQ ID NOS: 3 to 6 including antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In an embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate. phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/ or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes Tumor Protein 63 (p63).

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In an embodiment, the antisense oligonucleotides bind to the natural antisense sequences of Tumor Protein 63 (p63) and modulate the expression and/or function of p63 (SEQ ID NO: 1). Examples of antisense sequences include SEQ ID NOS: 2 to 6.

In an embodiment, the antisense oligonucleotides bind to one or more segments of Tumor Protein 63 (p63) polynucleotides and modulate the expression and/or function of p63. The segments comprise at least five consecutive nucleotides of the p63 sense or antisense polynucleotides.

In an embodiment, the antisense oligonucleotides are specific for natural antisense sequences of p63 wherein binding of the oligonucleotides to the natural antisense sequences of p63 modulate expression and/or function of p63.

In an embodiment, oligonucleotide compounds comprise sequences set forth as SEQ ID NOS: 3 to 6, antisense sequences which are identified and expanded, using for example, PCR, hybridization etc These oligonucleotides can comprise one or more modified nucleotides, shorter or longer fragments, modified bonds and the like. Examples of modified bonds or internucleotide linkages comprise phosphorothioate, phosphorodithioate or the like. In an embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding Tumor Protein 63 (p63), regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In an embodiment, the antisense oligonucleotides bind to coding and/or non-coding regions of a target polynucleotide and modulate the expression and/or function of the target molecule.

In an embodiment, the antisense oligonucleotides bind to natural antisense polynucleotides and modulate the expression and/or function of the target molecule.

In an embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative preferred target segments are considered to be suitable for targeting as well.

Target segments can include DNA or RNA sequences that comprise at least the 5 consecutive nucleotides from the 5'-terminus of one of the illustrative preferred target segments (the remaining nucleotides being a consecutive stretch of the same DNA or RNA beginning immediately upstream of the 5'-terminus of the target segment and continuing until the DNA or RNA contains about 5 to about 100 nucleotides). Similarly preferred target segments are represented by DNA or RNA sequences that comprise at least the 5 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, it is preferred to target specific nucleic acids by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise microRNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from so-called intergenic regions. The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and that either category is capable of regulating the corresponding sense transcripts—either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1:

In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2:

In the case of concordant regulation, one could concomitantly knock down both antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In an embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs). It is currently not known whether RNAa is conserved in other organisms.

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing via remodeling chromatin to thereby suppress transcription, degrading complementary mRNA, or blocking protein translation. However, in instances described in detail in the examples section which follows, oligonucleotides are shown to increase the expression and/or function of the Tumor Protein 63 (p63) polynucleotides and encoded products thereof. dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the "preferred target segments" identified herein may be employed in a screen for additional compounds that modulate the expression of Tumor Protein 63 (p63) polynucleotides. "Modulators" are those compounds that decrease or increase the expression of a nucleic acid molecule encoding p63 and which comprise at least a 5-nucleotide portion that is complementary to a preferred target segment. The screening method comprises the steps of contacting a preferred target segment of a nucleic acid molecule encoding sense or natural antisense polynucleotides of p63 with one or more candidate modulators, and selecting for one or more candidate modulators which decrease or increase the expression of a nucleic acid molecule encoding p63 polynucleotides, e.g. SEQ ID NOS: 3 to 6. Once it is shown that the candidate modulator or modulators are capable of modulating (e.g. either decreasing or increasing) the expression of a nucleic acid molecule encoding p63 polynucleotides, the modulator may then be employed in further investigative studies of the function of p63 polynucleotides, or for use as a research, diagnostic, or therapeutic agent in accordance with the present invention.

Targeting the natural antisense sequence preferably modulates the function of the target gene. For example, the p63 gene (e.g. accession number NM_001114979). In an embodiment, the target is an antisense polynucleotide of the p63 gene. In an embodiment, an antisense oligonucleotide targets sense and/or natural antisense sequences of p63 polynucleotides (e.g. accession number NM_001114979), variants, alleles, isoforms, homologs, mutants, derivatives, fragments and complementary sequences thereto. Preferably the oligonucleotide is an antisense molecule and the targets include coding and noncoding regions of antisense and/or sense p63 polynucleotides.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications. For example; such double-stranded moieties have been shown to inhibit the target by the classical hybridization of antisense strand of the duplex to the target, thereby triggering enzymatic degradation of the target.

In an embodiment, an antisense oligonucleotide targets Tumor Protein 63 (p63) polynucleotides accession number NM_001114979), variants, alleles, isoforms, homologs, mutants, derivatives, fragments and complementary sequences thereto. Preferably the oligonucleotide is an antisense molecule.

In accordance with embodiments of the invention, the target nucleic acid molecule is not limited to p63 alone but extends to any of the isoforms, receptors, homologs and the like of p63 molecules.

In an embodiment, an oligonucleotide targets a natural antisense sequence of p63 polynucleotides, for example, polynucleotides set forth as SEQ ID NOS: 2, and any variants, alleles, homologs, mutants, derivatives, fragments and complementary sequences thereto. Examples of antisense oligonucleotides are set forth as SEQ ID NOS: 3 to 6.

In one embodiment, the oligonucleotides are complementary to or bind to nucleic acid sequences of p63 antisense, including without limitation noncoding sense and/or antisense sequences associated with p63 polynucleotides and modulate expression and/or function of p63 molecules.

In an embodiment, the oligonucleotides are complementary to or bind to nucleic acid sequences of p63 natural antisense, set forth as SEQ ID NOS: 2 and modulate expression and/or function of p63 molecules.

In an embodiment, oligonucleotides comprise sequences of at least 5 consecutive nucleotides of SEQ ID NOS: 3 to 6 and modulate expression and/or function of p63 molecules.

The polynucleotide targets comprise p63, including family members thereof, variants of p63; mutants of p63, including SNPs; noncoding sequences of p63; alleles of p63; species variants, fragments and the like. Preferably the oligonucleotide is an antisense molecule.

In an embodiment, the oligonucleotide targeting p63 polynucleotides, comprise: antisense RNA, interference RNA (RNAi), short interfering RNA (shRNA); micro interfering RNA (miRNA); a small, temporal RNA (shRNA); or a short, hairpin RNA (shRNA); small RNA-induced gene activation (RNAa); or, small activating RNA (saRNA).

In an embodiment, targeting of Tumor Protein 63 (p63) polynucleotides, e.g. SEQ ID NOS: 2 modulate the expression or function of these targets. In one embodiment, expression or function is up-regulated as compared to a control. In an embodiment, expression or function is down-regulated as compared to a control.

In an embodiment, antisense compounds comprise sequences set forth as SEQ ID NOS: 3 to 6. These oligonucleotides can comprise one or more modified nucleotides, shorter or longer fragments, modified bonds and the like.

In an embodiment, SEQ ID NOS: 3 to 6 comprise one or more LNA nucleotides.

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript.

Because of their sequence-specificity, trans-cleaving enzymatic nucleic acid molecules show promise as therapeutic agents for human disease (Usman & McSwiggen, (1995) Ann. Rep. Med. Chem. 30, 285-294; Christoffersen and Marr, (1995) J. Med. Chem. 38, 2023-2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, (1979) Proc. R. Soc. London, B 205, 435) have been used to evolve new nucleic acid catalysts capable of catalyzing a variety of reactions, such as cleavage and ligation of phosphodiester linkages and amide linkages.

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min−1 in the presence of saturating (10 mM) concentrations of Mg2+ cofactor. An artificial "RNA ligase" ribozyme has been shown to catalyze the corresponding self-modification reaction with a rate of about 100 min−1. In addition, it is known that certain modified hammerhead ribozymes that have substrate binding arms made of DNA catalyze RNA cleavage with multiple turn-over rates that approach 100 min−1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987 (Uhlenbeck, O. C. (1987) Nature, 328: 596-600). The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences. This has allowed use of the catalytic RNA to cleave specific target sequences and indicates that catalytic RNAs designed according to the "hammerhead" model may possibly cleave specific substrate RNAs in vivo.

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In an embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type-molecule that doubles back on itself to form a duplex. Thus, the dsRNAs can be fully or partially double stranded. Specific modulation of gene expression can be achieved by stable expression of dsRNA hairpins in transgenic cell lines. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that this embodies' antisense compounds having antisense portions of 12, 13, 14, 15, 16, 17, 18, 19, 20, 21, 22, 23, 24, 25, 26, 27, 28, 29 or 30 nucleotides in length, or any range therewithin.

In an embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense Or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In an embodiment, the antisense oligonucleotides, such as for example, nucleic acid molecules set forth in SEQ ID NOS: 2 to 6 comprise one or more substitutions or modifications. In one embodiment, the nucleotides are substituted with locked nucleic acids (LNA).

In an embodiment, the oligonucleotides target one or more regions of the nucleic acid molecules sense and/or antisense of coding and/or non-coding sequences associated with p63 and the sequences set forth as SEQ ID NOS: 1 and 2. The oligonucleotides are also targeted to overlapping regions of SEQ ID NOS: 1 and 2.

Certain preferred oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased Uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one an embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleotides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5, 220,007; 5,256,775; 5,366,878; 5,403,711; 5,491,133; 5,565,350; 5,623,065; 5,652,355; 5,652,356; and 5,700,922, each of which is herein incorporated by reference.

In an embodiment, the region of the oligonucleotide which is modified comprises at least one nucleotide modified at the 2' position of the sugar, most preferably a 2'-O-alkyl, 2'-O-alkyl-O-alkyl or 2'-fluoro-modified nucleotide. In other an embodiment, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In an embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2—NH—O—CH2, CH, —N(CH3)-O—CH2 [known as a methylene(methylimino) or MMI backbone], CH2-O—N (CH3)-CH2, CH2-N(CH3)-N(CH3)-CH2 and O—N(CH3)-CH2-CH2 backbones, wherein the native phosphodiester backbone is represented as O—P—O—CH,). The amide backbones disclosed by De Mesmaeker et al. (1995) Acc. Chem. Res. 28:366-374 are also preferred. Also preferred are oligonucleotides having morpholino backbone structures (Summerton and Weller, U.S. Pat. No. 5,034,506). In other an embodiment, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone. Oligonucleotides may also comprise one or more substituted sugar moieties. Preferred oligonucleotides comprise one of the following at the 2' position: OH, SH, SCH3, F, OCN, OCH3OCH3, OCH3O(CH2)nCH3, O(CH2)nNH2 or O(CH2)nCH3 where n is from 1 to about 10; C1 to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator, a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH2CH2OCH3, also known as 2'-O-(2-methoxyethyl)]. Other preferred modifications include 2'-methoxy (2'-O—CH3), 2'-propoxy (2'-OCH2CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me—C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. A "universal" base known in the art, e.g., inosine, may be included. 5-Me—C substitutions have been shown to increase nucleic acid duplex stability by 0.6-1.2° C. and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety, an aliphatic chain, e.g., dodecandiol or undecyl residues, a polyaminc or a polyethylene glycol chain, or Adamantane acetic acid. Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the usc of LNA monomers to enhance the potency, specificity and duration of action and broaden the routes of administration of oligonucleotides comprised of current chemistries such as MOE, ANA, FANA, PS etc. This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Preferred modified oligonucleotide backbones comprise, but not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5, 177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide back bones; amide backbones; and others having mixed N, O, S and CH2 component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen, et al. (1991) Science 254, 1497-1500.

In an embodiment of the invention the oligonucleotides with phosphorothioate backbones and oligonucleosides with heteroatom backbones, and in particular —CH2-NH—O—CH2-, —CH2-N(CH3)-O—CH2- known as a methylene (methylimino) or MMI backbone, —CH2-O—N(CH3)-CH2-, —CH2N(CH3)-N(CH3)CH2- and —O—N(CH3)—CH2-CH2- wherein the native phosphodiester backbone is represented as —O—P—O—CH2- of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O alkyl-O-alkyl, wherein the alkyl, alkenyl and alkynyl may be substituted or unsubstituted C to CO alkyl or C2 to CO alkenyl and alkynyl. Particularly preferred are O (CH2)n OmCH3, O(CH2)n, OCH3, O(CH2)nNH2, O(CH2)nCH3, O(CH2)nONH2, and O(CH2nON(CH2)nCH3)2 where n and m can be from 1 to about 10. Other preferred oligonucleotides comprise one of the following at the 2' position: C to CO, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—CH2CH2OCH3, also known as 2'-O-(2-methoxyethyl) or 2'-MOE) i.e., an alkoxyalkoxy group. A further preferred modification comprises 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylamino-ethoxyethyl or 2'-DMAEOE), i.e., 2'-O—CH2-O—CH2-N(CH2)2.

Other preferred modifications comprise 2'-methoxy (2'-OCH3), 2'-aminopropoxy (2'-OCH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosinc, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al, 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rae-glycero-3-H-phosphonate, a polyamine or a polyethylene glycol chain, or Adarnantane acetic acid, a palmityl moiety, or an octadecylamine or hexylamino-carbonyl-toxycholesterol moiety.

Representative United States patents that teach the preparation of such oligonucleotides conjugates comprise, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Drug Discovery:

The compounds of the present invention can also be applied in the areas of drug discovery and target validation. The present invention comprehends the use of the compounds and preferred target segments identified herein in drug discovery efforts to elucidate relationships that exist between Tumor Protein 63 (p63) polynucleotides and a disease state, phenotype, or condition. These methods include detecting or modulating p63 polynucleotides comprising contacting a sample, tissue, cell, or organism with the compounds of the present invention, measuring the nucleic acid or protein level of p63 polynucleotides and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-Regulation or Inhibition of Gene Expression

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual antisense oligonucleotides would be assayed by modulation of the reporter gene. Reporter genes useful in the methods of the present invention include accetohydroxyacid synthase (AHAS), alkaline phosphatase (AP), beta galactosidase (LacZ), beta gluconanidase (GUS), chloramphenicol acetyl-transferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

p63 protein and mRNA expression can be assayed using methods known to those of skill. in the art and described elsewhere herein. For example, immunoassays such as the ELISA can be used to measure protein levels. p63 ELISA assay kits are available commercially, e.g., from R&D Systems (Minneapolis, Minn.).

In embodiments, p63 expression (e.g., mRNA or protein) in a sample (e.g., cells or tissues in vivo or in vitro) treated using an antisense oligonucleotide of the invention is evaluated by comparison with p63 expression in a control sample. For example, expression of the protein or nucleic acid can be compared using methods known to those of skill in the art with that in a mock-treated or untreated sample. Alternatively, comparison with a sample treated with a control antisense oligonucleotide (e.g., one having an altered or different sequence) can be made depending on the information desired. In another embodiment, a difference in the expression of the p63 protein or nucleic acid in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In embodiments, the level of p63 mRNA or protein, in a sample treated with an antisense oligonucicotide of the present invention, is increased or decreased by about 1.25-fold to about 10-fold or more relative to an untreated sample or a sample treated with a control nucleic acid. In embodiments, the level of p63 mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold. at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Kits, Research Reagents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the Tumor Protein 63 (p63) genes. These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays, SAGE (serial analysis of gene expression), READS (restriction enzyme amplification of digested cDNAs), TOGA (total gene expression analysis), protein arrays and proteomics, expressed sequence tag (EST) sequencing, subtractive RNA fingerprinting (SuRF), subtractive cloning, differential display (DD), comparative genomic hybridization, FISH (fluorescent in situ hybridization) techniques and mass spectrometry methods.

The compounds of the invention are useful for research and diagnostics, because these compounds hybridize to nucleic acids encoding Tumor Protein 63 (p63). For example, oligonucleotides that hybridize with such efficiency and under such conditions as disclosed herein as to be effective p63 modulators are effective primers or probes under conditions favoring gene amplification or detection, respectively. These primers and probes are useful in methods requiring the specific detection of nucleic acid molecules encoding p63 and in the amplification of said nucleic acid molecules for detection or for use in further studies of p63. Hybridization of the antisense oligonucleotides, particularly the primers and probes, of the invention with a nucleic acid encoding p63 can be detected by means known in the art. Such means may include conjugation of an enzyme to the oligonucleotide, radiolabeling of the oligonucleotide, or any other suitable detection means. Kits using such detection means for detecting the level of p63 in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of p63 polynucleotides is treated by administering antisense compounds in accordance with this invention. For example, in one non-limiting embodiment, the methods comprise the step of administering to the animal in need of treatment, a therapeutically effective amount of p63 modulator. The p63 modulators of the present invention effectively modulate the activity of the p63 or modulate the expression of the p63 protein. In one embodiment, the activity or expression of p63 in an animal is inhibited by about 10% as compared to a control. Preferably, the activity or expression of p63 in an animal is inhibited by about 30%. More preferably, the activity or expression of p63 in an animal is inhibited by 50% or more. Thus, the oligomeric compounds modulate expression of Tumor Protein 63 (p63) mRNA by at least 10%, by at least 50%, by at least 25%, by at least 30%. by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In one embodiment, the activity or expression of Tumor Protein 63 (p63) and/or in an animal is increased by about 10% as compared to a control. Preferably, the activity or expression of p63 in an animal is increased by about 30%. More preferably, the activity or expression of p63 in an animal is increased by 50% or more. Thus, the oligomeric compounds modulate expression of p63 mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the reduction of the expression of Tumor Protein 63 (p63) may be measured in scrum, blood, adipose tissue, liver or any other body fluid, tissue or organ of the animal. Preferably, the cells contained within said fluids, tissues or organs being analyzed contain a nucleic acid molecule encoding p63 peptides and/or the p63 protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexa-decyl-rac-glycero-3-Hphosphonate, a polyaminc or a polyethylene glycol chain, or Adamantane acetic acid, a palmityl moiety, or an octadecylamine or hexylamino-carbonyl-oxy-cholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansyl-sarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335, 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 3 to 6) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector, Adenovirus Vectors and Adeno-associated Virus Vectors.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refills to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer, intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid. Administration of antisense RNA into cerebrospinal fluid is described, e.g., in U.S. Pat. App. Pub. No. 2007/0117772, "Methods for slowing familial ALS disease progression," incorporated herein by reference in its entirety.

When it is intended that the antisense oligonucleotide of the present invention be administered to cells in the central nervous system, administration can be with one or more agents capable of promoting penetration of the subject antisense oligonucleotide across the blood-brain barrier. Injection can be made, e.g., in the entorhinal cortex or hippocampus. Delivery of neurotrophic factors by administration of an adenovirus vector to motor neurons in muscle tissue is described in, e.g., U.S. Pat. No. 6,632,427, "Adenoviral-vector-mediated gene transfer into medullary motor neurons," incorporated herein by reference. Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations.

The subject antisense oligonucleotides can also be linked or conjugated with agents that provide desirable pharmaceutical or pharmacodynamic properties. For example, the antisense oligonucleotide can be coupled to any substance, known in the art to promote penetration or transport across the blood-brain barrier, such as an antibody to the transferrin receptor, and administered by intravenous injection. The antisense compound can be linked with a viral vector, for example, that makes the antisense compound more effective and/or increases the transport of the antisense compound across the blood-brain barrier. Osmotic blood brain barrier disruption can also be accomplished by, e.g., infusion of sugars including, but not limited to, meso erythritol, xylitol, D(+) galactose, D(+) lactose, D(+) xylose, dulcitol, myo-inositol, L(−) fructose, mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," U.S. Pat. No. 6,294,520, "Material for passage through the blood-brain barrier," and U.S. Pat. No. 6,936,589, "Parenteral delivery systems," all incorporated herein by reference in their entirety.

The subject antisense compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTIN (available from GIBCO-BRL, Bethesda, Md.).

Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposomeslacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. diolcoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g. diolcoyltetramethylaminopropyl DOTAP and diolcoyl-phosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein by reference. Also preferred are combinations of penetration enhancers. for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bischlorocthyl-nitrosurca, busulfan, mitomycin C, actinomycin D, mithramycin, prednisone, hydroxyprogesterone, testosterone; tamoxifen, dacarbazine, procarbazine, hexamethylmelamine, pentamethylmelamine, mitoxantrone, amsacrine, chlorambucil, methylcyclohexylnitrosurca, nitrogen mustards, melphalan, cyclophosphamide, 6-mercaptopurine, 6-thioguanine, cytarabine, 5-azacytidine, hydroxyurca, deoxycoformycin, 4-hydroxyperoxycyclo-phosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of Tumor Protein 63 (p63), and the second target may be a region from another nucleotide sequence. Alternatively, compositions of the invention may contain two or more antisense compounds targeted to different regions of the same Tumor Protein 63 (p63) nucleic acid target. Numerous examples of antisense compounds are illustrated herein and others may be selected from among suitable compounds known in the art. Two or more combined compounds may be used together or sequentially.

Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

In embodiments, a patient is treated with a dosage of drug that is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100 mg/kg body weight. Certain injected dosages of antisense oligonucleotides are described, e.g., in U.S. Pat. No. 7,563,884, "Antisense modulation of PIP1B expression," incorporated herein by reference in its entirety.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1

Design of Antisense Oligonucleotides Specific for a Nucleic Acid Molecule Antisense to a Tumor Protein 63 (p63) and/or a Sense Strand of p63 Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95° C. to dissociate all pre-formed dsDNA complexes, then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's StepOne Plus Real Time PCR System or lightTyper instrument, Roche Diagnostics, Lewes, UK).

Melting peaks are constructed by plotting the negative derivative of fluorescence with respect to temperature (-d (Fluorescence)/dT) on the y-axis) against temperature (x-axis) using appropriate software (for example lightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40° C.

Example 2

Modulation of p63 Polynucleotides

Treatment of HEPG2 cells with Antisense Oligonucleotides
HepG2 cells from ATCC (cat#HB-8065) were grown in growth media (MEM/EBSS (Hyclone cat #SH30024, or Mediatech cat #MT-10-010-CV)+10% FBS (Mediatech cat#MT35-011-CV)+penicillin/streptomycin (Mediatech cat#MT30-002-CI)) at 37° C. and 5% $CO_2$. On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat#31985-070) and 4 μl of Lipofectamine 2000 (Invitrogen cat#11668019) at room temperature for 20 min and applied to each well of the 6 well plates with HEPG2 cells. A Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat#74181) following the manufacturers' instructions. 600 ng of RNA was added to the reverse transcription reaction performed using Verso cDNA kit from Thermo Scientific (cat#AB1453B) or High Capacity cDNA Reverse Transcription Kit (cat#4368813) as described in the manufacturer's protocol. The cDNA from this reverse transcription reaction was used to monitor gene expression by real time PCR using ABI Taqman Gene Expression Mix (car#4369510) and primers/probes designed by ABI (Applied Biosystems Taqman Gene Expression Assay: Hs00978340_m1 by Applied Biosystems Inc., Foster City Calif.). The following PCR cycle was used: 50° C. for 2 min, 95° C. for 10 min, 40 cycles of (95° C. for 15 seconds, 60° C. for 1 min) using Mx4000 thermal cycler (Stratagene). Fold change in gene expression after treatment with antisense oligonucleotides was calculated based on the difference in 18S-normalized dCt values between treated and mock-transfected samples.

Results:
Real time PCR results show that the levels of p63 mRNA are significantly increased in HepG2 cells 48 h after treatment with one antisense oligonucleotide to p63 natural antisense Hs.553263 (FIG. 1).

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A method of upregulating a function of and/or the expression of a Tumor Protein 63 (p63) polynucleotide having SEQ ID NO: 1 or an isoform of p63 in mammalian cells or tissues in vivo or in vitro comprising:
contacting said cells or tissues with at least one antisense oligonucleotide of 12 to 30 nucleotides in length that specifically targets a region of a natural antisense polynucleotide of the Tumor Protein 63 (p63) gene having SEQ ID NO: 2; thereby upregulating a function of and/or the expression of the Tumor Protein 63 (p63) polynucleotide in mammalian cells or tissues in vivo or in vitro.

2. The method of claim 1, wherein a function of and/or the expression of the Tumor Protein 63 (p63) is increased in vivo or in vitro with respect to a control.

3. The method of claim 1, wherein the at least one antisense oligonucleotide targets a natural antisense polynucleotide that is antisense to coding and/or non-coding nucleic acid sequences of a Tumor Protein 63 (p63) RNA polynucleotide transcribed by the p63 gene.

4. The method of claim 1, wherein the at least one antisense oligonucleotide targets a natural antisense polynucleotide having overlapping and/or non-overlapping sequences with a Tumor Protein 63 (p63) RNA polynucleotide transcribed from the p3 gene.

5. The method of claim 1, wherein the at least one antisense oligonucleotide comprises one or more modifications selected from: at least one modified sugar moiety, at least one modified internucleoside linkage, at least one modified nucleotide, and combinations thereof.

6. The method of claim 5, wherein the one or more modifications comprise at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and combinations thereof.

7. The method of claim 5, wherein the one or more modifications comprise at least one modified internucleoside linkage selected from: a phosphorothioate, alkylphosphonate, phosphorodithioate, alkylphosphonothioate, phosphoramidate, carbamate, carbonate, phosphate triester, acetamidate, carboxymethyl ester, and combinations thereof.

8. The method of claim 5, wherein the one or more modifications comprise at least one modified nucleotide selected from: a peptide nucleic acid (PNA), a locked nucleic acid (LNA), an arabino-nucleic acid (FANA), an analogue, a derivative, and combinations thereof.

9. The method of claim 1, wherein the at least one oligonucleotide comprises oligonucleotide SEQ ID NO: 5.

10. A method of upregulating a function of and/or the expression of a Tumor Protein 63 (p63) gene in mammalian cells or tissues in vivo or in vitro comprising:
contacting said cells or tissues with at least one short interfering RNA (siRNA) oligonucleotide 19 to 30 nucleotides in length, said at least one siRNA oligonucleotide being specific for a overlapping region of a natural antisense polynucleotide of a Tumor Protein 63 (p63) polynucleotide having SEQ ID NO: 2; and, upregulating a function of and/or the expression of Tumor Protein 63 (p63) in mammalian cells or tissues in vivo or in vitro.

11. A method of upregulating a function of and/or the expression of Tumor Protein 63 (p63) having SEQ ID NO: 1 or an isoform thereof in mammalian cells or tissues in vivo or in vitro comprising:
contacting said cells or tissues with at least one antisense oligonucleotide of about 10 to 30 nucleotides in length specific for a natural antisense polynucleotide of a Tumor Protein 63 (p63) polynucleotide having SEQ ID NO: 2 wherein said at least one antisense oligonucleotide has at least 80% sequence identity to at least one nucleic acid sequence set forth as SEQ ID NOS: 1 or an RNA polynucleotide encoded by the p63 gene; and, upregulating the function and/or expression of the Tumor Protein 63 (p63) in mammalian cells or tissues in vivo or in vitro.

12. A method of upregulating the expression of Tumor Protein 63 (p63) transcript variant 3 polynucleotide or an isoform thereof and/or at least one encoded product thereof in a mammal, comprising:

administering to said mammal a dose of at least one antisense oligonucleotide of about 10 to 30 nucleotides in length that specifically binds to a natural antisense polynucleotide of said at least one Tumor Protein 63 (p63) polynucleotide having SEQ ID NO: 2 and upregulates expression of said at least one Tumor Protein 63 (p63) polynucleotide; thereby upregulating the at least one Tumor Protein 63 (p63) polynucleotide and/or at least one encoded product thereof wherein the mammal has a skin condition or disorder or cancer.

* * * * *